United States Patent [19]

Duncan et al.

[11] Patent Number: 5,354,429
[45] Date of Patent: Oct. 11, 1994

[54] NATURAL CRESYLIC ACID PROCESSING

[75] Inventors: David H. Duncan, Mandan; Gene G. Baker, Hazan; Dana J. Maas, Golden Valley; Kevin M. Mohl, Hazen; Robert G. Todd, Dickinson, all of N. Dak.

[73] Assignee: Dakota Gasification Company, Beulah, N. Dak.

[21] Appl. No.: 86,753

[22] Filed: Jul. 2, 1993

Related U.S. Application Data

[63] Continuation of Ser. No. 802,221, Dec. 4, 1991, abandoned.

[51] Int. Cl.$^5$ .................... B01D 3/14; B01D 3/40; C07C 37/74; C07C 37/80
[52] U.S. Cl. ..................... 203/59; 203/64; 203/78; 203/DIG. 9; 568/751; 568/756; 568/759; 568/761
[58] Field of Search .................... 203/59, 63, 64, 78, 203/DIG. 9; 568/751, 759, 756, 761; 208/41

[56] References Cited

U.S. PATENT DOCUMENTS

| | | | |
|---|---|---|---|
| 2,618,666 | 11/1952 | Hess et al. | 568/756 |
| 2,666,796 | 1/1954 | Gorin et al. | 568/761 |
| 2,767,220 | 10/1956 | Neuworth | 568/759 |
| 2,789,145 | 4/1957 | Neuworth | 568/759 |
| 2,969,401 | 1/1961 | Young et al. | 568/751 |
| 3,075,890 | 1/1963 | Chambers et al. | 203/64 |
| 3,169,101 | 2/1965 | Berthoux et al. | 203/59 |
| 3,331,755 | 7/1967 | Neuworth | 203/59 |
| 3,827,947 | 8/1974 | Melpolder et al. | 203/64 |
| 3,830,708 | 8/1974 | Karhan et al. | 203/64 |
| 4,429,170 | 1/1984 | Lovell | 568/759 |
| 4,443,636 | 4/1984 | Greco | 568/759 |
| 4,487,987 | 12/1984 | Paslean et al. | 568/756 |
| 4,503,267 | 3/1985 | Pavlin | 568/753 |

FOREIGN PATENT DOCUMENTS

| | | |
|---|---|---|
| 204474 | 3/1982 | Fed. Rep. of Germany . |
| 433-6461 | 11/1983 | Fed. Rep. of Germany . |
| 3302812A1 | 8/1984 | Fed. Rep. of Germany . |
| 678191 | 8/1952 | United Kingdom . |
| 708925 | 5/1954 | United Kingdom . |
| 730473 | 5/1955 | United Kingdom . |

OTHER PUBLICATIONS

Chemical Abstracts, vol. 115, No. 24, 16 Dec. 1991 Columbus, OH, US; abstract No. 259728b, K. K. Tiwari et al. 'Extraction of tar acids with glycols,' p. 217; column 1.
Pavlin, *Chem. Abstr.*, vol. 102:204131c, 1985.
Heinrich, *Chem. Abstr.*, vol. 102:24274t, 1985.
Tiwari, *Chem. Abstr.*, vol. 99:56151m, 1983.
Szozda, *Chem. Abstr.*, vol. 95:6694n, 1981.
Bhaduri, *Chem. Abstr.*, vol. 81:66005j, 1974.
Raj, *Chem. Abstr.*, vol. 73:68334z, 1970.
Waddington, abstract of UKP 969,013, Sep. 9, 1964, *Chem. Abstr.*, p. 13094, 1964.
Aarna, *Chem. Abstr.*, vol. 58, p. 10788, 1963.
Higuchi, *Chem. Abstr.*, vol. 54, p. 25706, 1960.
Kulik, *Chem. Abstr.*, vol. , p. 9254, 1960.
Kubicka, *Chem. Abstr.*, vol. 51, p. 8037, 1960.
Kozaki, *Chem. Abstr.*, vol. , p. , 1960.
Ishida, *Chem. Abstr.*, vol. 48, p. 7283, 1954.
Ishida, *Chem. Abstr.*, vol. 48, p. 9045, 1954.
Fuchi, *Chem. Abstr.*, vol. 46, p. 7740, 1952.
Funusaka, *Chem. Abstr.*, vol. , p. 9138, 1950

(List continued on next page.)

*Primary Examiner*—Virginia Manoharan
*Attorney, Agent, or Firm*—Chilton, Alix & Van Kirk

[57] ABSTRACT

A discrete impure cresylic acid distillate fraction derived by fractional distillation of a natural cresylic acid feedstock from which tar bases and/or neutral oils have not been removed is subjected to extractive distillation with a polyhydric alcohol extractant and subsequent separation of the discrete cresylic acid fraction. The extractive distillation removes tar bases, neutral oils, undesirable phenolic substances, sulfur compounds, color-forming impurities and odor-imparting impurities.

6 Claims, No Drawings

OTHER PUBLICATIONS

Prutton, *Chem. Abstr.*, vol. 44, p. 7514, 1950.
Noji, *Chem. Abstr.*, vol. 54, p. 25706, 1960.
Zaheer, *Chem. Abstr.*, vol. 54, p. 2832, 1960.
Berber, *Chem. Abstr.*, vol. 79:94595d, 1973.
Bhaduri, *Chem. Abstr.*, vol. 67:101705x, p. 9594, 1967.
Nair, *Chem. Abstr.*, vol. 67:4779s, p. 459, 1967.
Nair, *Chem. Abstr.*, vol. 64, p. 4832, 1966.
Waddington, *Chem. Abstr.*, vol. 64, p. 14004, 1966.
Zidkowski, *Chem. Abstr.*, vol. 62, p. 15953, 1965.
Ziolkowski, *Chem. Abstr.*, vol. 62, p. 7560, 1965.
Neuworth, *Chem. Abstr.*, vol. 61, p. 11812, 1964.
Sen, *Chem. Abstr.*, vol. 61, p. 5417, 1964.
Neuworth, *Chem. Abstr.*, vol. , p. 13666, 1963.
Stuckey, *Chem. Abstr.*, vol. , p. 15889, 1961.
Batchelder, *Chem. Abstr.*, vol. , p. 9254, 1960.
Kozaki, *Chem. Abstr.*, vol. 53, p. 13553, 1959.
Gorin, *Chem. Abstr.*, vol. , p. 5470, 1954.
Saunier, *Chem. Abstr.*, vol. 46, p. 6152, 1952.
Neuworth, *Chem. Abstr.*, vol. , p. 238, 1952.
Molinari, *Chem. Abstr.*, vol. , p. 7590, 1940.
Gogoleva, *Chem. Abstr.*, vol. 68:61344r, 1968.
Heyberger, *Chem. Abstr.*, vol. 98:74257j, 1983.
Jastrzebski, *Chem. Abstr.*, vol. 87:55575t, 1977.
D'yakova, *Chem. Abstr.*, vol. 63, p. 6756, 1965.
Schmidt, German Pat. No. 1,144,287, *Chem. Abstr.*, vol. , p. , 1963.
Ulbricht, *Chem. Abstr.*, vol. 57, p. 10123, 1962.
Bemmann, *Chem. Abstr.*, vol. 55, p. 21552, 1961.
Höfling, *Chem. Abstr.*, vol. 55, p. 21550, 1961.
Hansen, *Chem. Abstr.*, vol. 54, p. 5572, 1960.
Preiss, *Chem. Abstr.*, vol. 54, p. 15892, 1960.
Doughty, *Chem. Abstr.*, vol. 46, p. 6815, 1952.
Shibayama, *Chem. Abstr.*, vol. 110:216186c, 1989.
Shimizu, *Chem. Abstr.*, vol. 110:216185b, 1989.
Kunitake, *Chem. Abstr.*, vol. 106:70175s, 1987.
Ishii, *Chem. Abstr.*, vol. 107:136316t, 1987.
Spengler, *Chem. Abstr.*, vol. 104:111779w, 1986.
Hoeringklee, *Chem. Abstr.*, vol. 102:45616w, 1985.
Markus, *Chem. Abstr.*, vol. 97:26131w, 1982.
Jagirder, *Chem. Abstr.*, vol. 96:106126t, 1982.
Malinowski, *Chem. Abstr.*, vol. 90:124470f, 1979.
Malinowski, *Chem. Abstr.*, vol. 87:134234j, 1977.
Ruehl, *Chem. Abstr.*, vol. 85:20946w, 1976.
Maczynski, *Chem. Abstr.*, vol. 79:53008w, 1973.
Gorin, *Chem. Abstr.*, vol. 69:29153n, 1968.
Holdsworth, *Chem. Abstr.*, vol. 68:40521f, 1968.
Matsumoto, *Chem. Abstr.*, vol. 67:66436m, p. 66442, 1967.
Strobach, *Chem. Abstr.*, vol. 63, p. 6756, 1965.
Schäfer, *Chem. Abstr.*, vol. 53, p. 17057, 1959.
JP-A-02204470, Aug. 14, 1990 (abstract).
Mahapatra, *Chem. Abstr.*, vol. 109:210227z, 1988.
Mendiratta, *Chem. Abstr.*, vol. 104:168111b, 1986.
JP-A-62056448, Mar. 12, 1987 (abstract).
Kostyuk, *Chem. Abstr.*, vol. 102:187800a, 1985.
Leston, *Chem. Abstr.*, vol. 102:166461a, 1985.
Kiva, *Chem. Abstr.*, vol. 102:203714h, 1985.
Zudkevitch, *Chem. Abstr.*, vol. 100:70335v, 1984.
Leston, *Chem. Abstr.*, vol. 100:191564c, 1984.
Hoeringklee, *Chem. Abstr.*, vol. 100:191566e, 1984.
Leston, *Chem. Abstr.*, vol. 101:23128r, 1984.
JP Kokai 58,131,928, *Chem. Abstr.*, vol. 100:22404v, 1984.
Deetman, *Chem. Abstr.*, vol. 99:70376v, 1983.
Kostyuk, *Chem. Abstr.*, vol. 96:199212f, 1982.
JP Kokai, 81,115,731, *Chem. Abstr.*, vol. 95:203545r, 1981.
Dodd, *Chem. Abstr.*, vol. 94:191926e, 1981.
Wuest, *Chem. Abstr.*, vol. 94:15390s, 1981.
Takahata, *Chem. Abstr.*, vol. 94:30349d, 1981.
JP Kokai 81 46,829, *Chem. Abstr.*, vol. 95:132485h, 1981.
JP Kokai 81 45,431, *Chem. Abstr.*, vol. 95:97363t, 1981.
Wadekar, vol. 95:132401c, 1981.
JP-A-56065834, Jun. 3, 1981 (abstract).
Welch, *Chem. Abstr.*, vol. 87:25344z, 1977.
Maxwell, *Chem. Abstr.*, vol. 87:5634r, 1977.
Tesar, *Chem. Abstr.*, vol. 84:89818c, p. 89821, 1976.
Suzuki, *Chem. Abstr.*, vol. 84:105201d, 1976.
Kiva, *Chem. Abstr.*, vol. 83:137706t, 1975.
Melpolder, *Chem. Abstr.*, vol. 81:120205q, 1974.
Yonemitsu, *Chem. Abstr.*, vol. 81:3578c, 1974.
Karhan, *Chem. Abstr.*, vol. 81:104994r, 1974.
Nagakura, *Chem. Abstr.*, vol. 78:159186x, 1973.
Turbin, *Chem. Abstr.*, vol. 76, 72218u, 1972.
UKP 1,254,139, *Chem. Abstr.*, vol. 76:45926s, 1972.
Anazawa, *Chem. Abstr.*, vol. 70:105720h, 1969.
Anazawa, *Chem. Abstr.*, vol. 70:77489u, 1969.
Schlichting, *Chem. Abstr.*, vol. 70:11340g, 1969.
Kostyuk, *Chem. Abstr.*, vol. 70:70035j, 1969.
UKP 1,067,900, *Chem. Abstr.*, vol. 68:68674g, 1968.
Neuworth, *Chem. Abstr.*, vol. 68:49286r, 1968.

(List continued on next page.)

OTHER PUBLICATIONS

Neuworth, *Chem. Abstr.*, vol. 67:83761f, 1967.
Bhaduri, *Chem. Abstr.*, vol. 67:101705x, 1967.
Welch, *Chem. Abstr.*, vol. 65, p. 10400, 1966.
Waddington, *Chem. Abstr.*, vol. 64. p. 14004, 1966.
Aarna, *Chem. Abstr.*, vol. 63, p. 17994, 1965.
French Pat. No. 1,396,197, *Chem. Abstr.*, vol. 63, p , 1965.
Binder, *Chem. Abstr.*, vol. 60, p. 2835, 1964.
Bondy, UKP 890,642 *Chem. Abstr.*, vol. 57, p. , 1962.
State German Pat. No. 967,075, *Chem. Abstr.*, vol. 53, p. 17480, 1959.
Kozaki, *Chem. Abstr.*, vol. 53, p. 13553, 1959.
Kennard, Australian Pat. No. 147,351, *Chem. Abstr.*, vol. 51, p. 12473, 1957.
Tishchenko, *Chem. Abstr.*, vol. 51, p. 1068, 1957.
Neuworth, *Chem. Abstr.*, vol. 51, p. 12473, 1957.
UKP 708,925, *Chem. Abstr.*, vol. 48, p. 8254, 1954.
Parant, *Chem. Abstr.*, vol. 47, p. 934, 1953.
Golumbic, *Chem. Abstr.*, vol. 43. 7788, 1949.
Sventsitskil, *Chem. Abstr.*, vol. 31, p. 2785, 1937.
Australian Pat. No. 147,351, *Chem. Abstr.*, vol. 51, p. 12473, 1957.

Woehler, "Dephenolation of Effluents", Br. Carbonisation Res. Assoc., Spec. Publ., vol. 24, pp. 46–51, 1979.
Forbath, "Process Flowsheet", *Chem. Engr.*, 228–231, Jul. 1957.

Lurgi advertisement for Phenosolvan and Phenoraffin processes.

NATURAL CRESYLIC ACID PROCESSING

This is a continuation of copending application Ser. No. 07/802,221 filed Dec. 4, 1991 now abandoned.

Field of the Invention

Impurities are removed from discrete distillate fractions derived from cresylic acid ($C_6$ through $C_9$ alkylphenol) mixtures. Extractive distillation with polyhydric alcohols is capable of removing virtually all impurities found in raw cresylic acid distillate fractions, such as phenol, ortho-cresol, meta/para-cresol, 2,4/2,5-xylenol and mixtures of the higher-boiling xylenols (HBX), ethylphenols and $C_9$ phenols.

BACKGROUND

All of the so-called natural cresylic acid feedstocks (containing phenol, cresols, ethylphenols, xylenols and $C_9$ phenolics) are derived from either coal or petroleum processing. Petroleum refinery "spent caustic" is derived via extraction (with aqueous sodium hydroxide) of phenols and thiophenols (along with traces of neutral oils and tar bases) from oil refinery distillate products. Neutral oil (as used throughout this text) is a class of organic impurities (indigenous to natural cresylic acid feedstocks), each one of which is neither an acid nor a base, such as indenes, indans, ketones and naphthalenes. Tar bases (as used throughout this text) constitute a class of organic impurities (indigenous to natural cresylic acid feedstock), each member of which is a nitrogen-containing compound which behaves as a base, such as pyridine, alkylpyridine, aniline and alkylaniline.

Processing of spent caustic into purified cresylic acid usually consists of two or three steps: one for separation of sulfur compounds from phenols, a second step (sometimes omitted) for separation of neutral oil substances and tar bases via a steam distillation step to steam them from the caustic solution and a final (third) step (always included) to neutralize the sodium cresylate with an acid or acid gas in order to "spring" the free phenols (liberate them as an oil phase). Such purified cresylic acid mixtures, after drying and depitching, are either sold as such, or they are fractionated into various products, such as phenol, ortho-cresol, meta/para-cresol, 2,4/2,5-xylenol and high boiling xylenol/ethylphenol/$C_9$ phenol mixtures.

Such a process provides a raw cresylic acid feedstock suitable for the subject process, provided the steaming step for removal of tar bases and neutral oil is either eliminated or reduced in severity. (As used in the text and claims, "raw" refers to dried and depitched material from which tar bases and neutral oils have not been removed.)

Coal-derived feedstocks come from coal process technologies, such as coking, gasification or other coal devolatilization processes. All such coal technologies yield at least two condensate streams: 1) coal tar oil (to be discussed first) and 2) phenolic-rich condensate water (to be discussed later). Both of these materials result from cooling gaseous devolatilization products from heating of coal; they are condensates.

Coal tar oil is useful as a feedstock for manufacturing cresylic acid (among other products). A typical coal tar oil contains moisture (2% to 5%), naphtha (5% to 10%), middle oil distillate, also known as carbolic oil distillate or tar oil distillate (30% to 40%) and a distillation bottoms product somewhat resembling creosote, the balance.

The middle oil (or carbolic oil) distillate fraction (from coal tar oil), which is useful for manufacturing cresylic acid, is made up of phenolics (30% to 40%), neutral hydrocarbons (approximately 60% to 70%) and tar bases (1% to 3%). This material can be processed into either finished cresylic acid mixtures or raw, impure cresylic acid mixtures by any of a number of techniques.

The oldest of all these technologies was developed in the late 1800's. This process utilized a sodium hydroxide solution to extract phenols from neutral hydrocarbon oils. The caustic extract was decanted from the majority of the neutral hydrocarbons (which formed a separate phase). Inevitably some neutral oil substances and the majority of the tar bases present in the middle oil were extracted into the caustic solution. The caustic solution of phenols was then heated in order to steam distill these two classes of impurities, neutral oils and tar bases. In practice, this steaming step has never been pushed hard enough to remove all of these impurities. The purified aqueous sodium phenolate solution was then reacted with carbon dioxide by sparging stack gas into the solution. The carbon dioxide reacted with the sodium salt of the phenols to form free cresylic acid (an oil phase) and a sodium carbonate solution (an aqueous phase). The aqueous phase was separated from the sprung phenols by decantation, and then reacted with quicklime to regenerate sodium hydroxide for recycle. The sprung phenols were then dried via distillation of moisture, and then depitched via distillation to separate the purified cresylic acid from any pitch-like substances formed during the steam distillation step.

The product of this process is useful as finished cresylic acid, or it can be fractionated into finished cresylic acid distillate products.

If the steaming step to remove tar bases and residual neutral oil were either eliminated or reduced in severity, the sprung, dried and depitched raw cresylic acid would be a suitable feedstock for the subject process.

This oldest technology has some significant disadvantages. It is bulky and energy intensive, and it creates waste streams and materials which are hazardous and difficult to remediate. For this reason, chemists and engineers went on to develop solvent extraction technologies to separate neutral oil from phenolic substances. These solvent technologies were inferior in at least one regard to the earliest technology, since the latter separated both neutral oil and tar bases.

Many of the numerous solvent extraction technologies (developed since this earliest technique) employed the use of a single solvent to extract phenols from a neutral oil (middle oil) matrix. Aqueous solutions of a number of solvents, such as glycols, ethanolamine, ammonia, acetic acid, ethylamine, sodium salicylate and methanol, were employed. Hot water was another single-solvent approach which was used. The solvents were usually removed from the extract mixture by way of distillation and recycled to the front end of the process. All of these technologies were faced with the problem of obtaining adequate cresylic acid product purity. The phenols which were isolated via these technologies contained significant amounts of residual neutral oil contaminants and tar bases. This problem was especially prevalent when a high yield (degree of recovery) was obtained: with high product yields it was inevitable that large amounts of neutral oil and tar base impurities would be found in the phenolic extract (solvent) phase. Any of these single-solvent processes would provide a raw cresylic acid ready for fractionation into impure distillate fractions suitable for the subject process. Significant amounts of such impurities pose no problem for said process.

Because of the purity vs. yield problems of the single-solvent techniques, chemists and engineers went on to develop dual-solvent (fractional countercurrent extraction) techniques. These technologies provided the ability to obtain high purity and high yield at once, by using a pair of solvents; one, a polar solvent to dissolve the phenols, and another, a non-polar solvent to dissolve the neutral oil impurities. Examples of polar solvents are aqueous solutions of a number of solvents, including methanol, ammonia, acetamide, acetic acid, ethanol, monoethylamine, sodium salts of sulfonic acids, etc.; and examples of non-polar solvents include hexane, heptane, petroleum ether, diesel and various non-aromatic naphthas. Distillation techniques were used to regenerate both polar and non-polar solvents for recycle.

Like the single solvent techniques, none of these technologies could achieve a good separation of tar bases from phenols; only neutral oil substances were separated. The cresylic acid materials derived from dual solvent processing required another treatment step to remove tar bases prior to sale as a mixed cresylic acid finished product or prior to fractionation for finished distillate products.

Any of these dual solvent technologies could be used to obtain a raw cresylic acid which would be suitable for the subject invention. Indeed, any of these processes could be operated (for purposes of the present invention) in a most economical fashion (such that neutral oil substances would not be thoroughly removed), since the instant technology can easily handle significant amounts of these substances.

Other types of dual solvent-like processes which were developed were the Phenoraffin process and others similar to it. In this technology, saturated aqueous sodium cresylate served as the polar solvent, and toluene (or the like) in a second extraction step was comparable to the non-polar solvent. The sodium cresylate solution, which became "oversaturated" with dissolved free phenols, was boiled in order to steam distill toluene, and some of the neutral oil not removed in the primary extraction steps. A solvent, such as diisopropyl ether, was then used to extract the free phenols from the sodium cresylate solution, thus regenerating it for recycle to the front end of the process. The isopropyl ether solution of the phenols was then extracted with aqueous sulfuric acid to remove tar bases, and finally the ether was distilled for recycle, leaving the purified phenols (ready for drying and depitching) as a still-bottoms product.

This process, if 1) operated in a most economical fashion (such that it would not remove all of the neutral oil), and if 2) the sulfuric acid step were eliminated, would yield a raw cresylic acid mixture suitable for the subject process.

The East Germans developed technologies based upon the use of calcium hydroxide for purification of cresol mixtures. Cresols were mixed with water, heated, and then reacted with calcium hydroxide to form the calcium cresolate salt (water soluble). The Leuna Werke plant in East Germany patented such a process in 1962 for removal of neutral oil from cresols (British Patent No. 895,119). This aqueous salt was filtered and then further diluted with water to cause neutral oils to be "sprung" from the solution as a black oily liquid (neutral oil substances are less soluble in dilute aqueous calcium cresolate solution than in a more concentrated solution). The product cresolate solution was then acidified with hydrochloric acid in order to spring the cresols, making them ready for drying and depitching.

In order for this process to be implemented in a more economical fashion, the amount of water used to dilute the calcium cresolate solution (to spring the neutral oil, the black oily liquid) could be diminished (or eliminated altogether). In this way, the product (cresols) would be less pure, but would be suitable as raw cresols for the subject process.

Since few of the foregoing technologies were capable of removing tar bases, a number of tar base removal processes were developed. The most elementary (and probably most common) was a process which could be called the acid flash distillation process. Sulfuric (or less commonly phosphoric) acid was added to cresylic acid (or a fraction thereof in some few instances), and this mixture was distilled in either a batch still or a continuous flash drum. The tar bases were rendered non-volatile via salt formation with the sulfuric acid, and were collected as a still-bottoms product. The overhead product was obtained as a very nearly tar-base-free material.

The Leuna Werke plant in East Germany, which (in 1984) patented a glycol-based extractive distillation process to remove guaiacol from meta/para-cresol, developed a unique version of the acid flash process, also patented in 1984. They removed tar bases from phenols by adding sulfuric acid to the fractionation tower while it was being used to fractionate the distillate products (such as meta/para-cresol) which can be manufactured from cresylic acid.

Another variation of the acid flash process was developed in Poland. It was very similar to the continuous version of the traditional acid flash method, except that water was used in the distillation to limit the temperature of the process (and thus limit the degradation of phenols to tar-like residue).

An earlier West German patent for removal of tar bases described a process wherein a cresylic acid distillate fraction was mixed with a strong acid and some toluene (or other aromatic) and cooked for a time. This was followed by a distillation wherein the overhead product, cresylic acid, was treated with activated alumina. The tar base/toluene condensation products were removed as a still-bottoms product.

In an East Indian dissociative extraction process, cresylic acid was dissolved in a solvent, such as chlorobenzene or 2-ethylhexanol, and this mixture was extracted in a countercurrent fashion with aqueous hydrochloric acid. The solvent was distilled from the phenols and recycled. Tar bases were removed from the extraction column as the hydrochloride salts.

Patents have also been granted for the use of strongly acidic cation exchange resins to remove tar bases from cresylic acid. Similarly, the Japanese have patented the use of acidic clays to remove traces of tar bases from cresylic acid.

All of the above tar base removal techniques were developed as an adjunct step to supplement a neutral oil removal step.

All of the above descriptions of processes for removal of neutral oil and tar bases were cited (for purposes of this document) in the context of tar oil (or middle oil) distillate processing.

As noted earlier, the condensate water stream which results from cooling of gaseous coal devolatilization products is rich in dissolved phenolics. Such aqueous condensate (gas liquor) streams are typically subjected to a solvent extraction process in order to extract the phenols from the water, as is well known in the art. The solvent is then distilled from the phenols and recycled. Typical of these process technologies is the Phenosolvan process, which utilizes diisopropyl ether or a similar solvent as the extraction solvent.

A typical Phenosolvan extract mixture of phenols (known as crude phenol) usually contains approximately 60 to 75% monohydric phenols (cresylic acid) and also contains dihydric phenols (such as catechol) and pitch (20% to 25%), neutral oil (1% to 4%), tar bases (1% to 3%) and water (2% to 6%).

Processing of phenolic extracts derived from such wastewater should first include a process step for separation of the monohydric phenols from the dihydric phenols and pitch. This separation is typically accomplished by way of a distillation (depitching) step. Initial processing should also include a drying step for separation of water via distillation. The monohydric phenols cut, thus isolated, is a fairly pure material compared to middle oil distillate; it contains only 1.5 to 4% tar bases and 1.5 to 5% neutral oil. Such material 1) can be processed via any of the earlier-described neutral oil and tar base removal techniques designed for the far less pure tar oil distillate mixtures, or 2) can be blended with tar oil distillate and processed by any of these same earlier-described techniques.

The cresylic acid industry in the past focused almost exclusively upon purification technologies which treat a broad boiling-range mixture of phenols ($C_6$ through $C_9$) in order to render such mixtures free of the two principal classes of contaminants indigenous to natural cresylic acid mixtures (both coal and petroleum-derived): neutral oil and tar bases. Once free of these impurities, cresylic acid mixtures were either sold as such, or fractionated into distillate products and then sold. At times such distillate products were processed for even further upgrading.

Such further upgrading (of the individual distillate fractions from natural cresylic acid mixtures) almost exclusively dealt with the topic of further separations of phenolic substances from one another (which cannot be accomplished via ordinary fractionation techniques). Feedstocks for such phenolic separation technologies have been distillate fractions derived via fractionation of tar-base- and neutral-oil-free phenolic mixtures.

Consolidation Coal (later known as Pitt-Consol) patented glycol extractive distillation for removal of 2,6-xylenol, an unwanted phenolic substance, from m/p-cresol (a discrete distillate fraction derived from cresylic acid). This process was described in their 1967 patent (U.S. Pat. No. 3,331,755) granted to Martin Neuworth, assigned to Consolidation Coal Co.

Pitt-Consol used the acid flash process for removal of tar bases from a wide boiling range mixture of phenols prior to fractionation to isolate the m/p-cresol distillate fraction. Earlier, under the name of Consolidation Coal, they used the dual solvent technology described in U.S. Pat. Nos. 2,666,796 and 3,079,326 for removal of neutral oil from a coal-derived middle oil distillate (a wide boiling range mixture). (It should be noted that Pitt-Consol later used a similar dual solvent technology to process oil refinery spent caustic-derived cresylic acid; see U.S. Pat. Nos. 2,767,220 and 2,789,145.) The m/p-cresol described in U.S. Pat. No. 3,331,755 was thus tar-base and neutral-oil free.

Extractive distillation of a cresylic acid fraction with glycols was also described in East German Patent No. DD 204,474, granted to the Leuna Werke plant for removal of guaiacol from m/p-cresol via glycol extractive distillation. This patent also described the partial removal of ortho-ethylphenol from m/p-cresol. As noted earlier, 1) Leuna Werke patented a calcium salt technique for removal of neutral oil from cresols, and 2) they also patented the use of sulfuric acid to remove tar bases in-situ during fractionation. Based on these patents, the m/p-cresol described in East German Patent No. DD 204,474 is thus tar-base and neutral-oil free.

SUMMARY OF INVENTION

Extractive distillation using a polyhydric alcohol, such as a glycol, or another functionally similar substance is a much more versatile purification technique for materials derived from natural cresylic acid feedstocks than previously described. Prior art teaches that guaiacol and 2,6-xylenol can be removed from m/p-cresol (a distillate fraction from natural cresylic acid), and that ortho-ethylphenol can be partially removed from the same by means of this technique.

We have found that this process is also capable of removing tar base substances and neutral oil substances from any of the discrete distillate fractions of natural cresylic acid. The tendency of the phenolic substances (in any of the distillate fractions from cresylic acid) to hydrogen bond with diols, such as glycols or other polyhydric alcohols, results in a decrease in the volatility of these phenolics. (Throughout the text and claims "phenols" and "phenolics" are used interchangeably.) Without exception, tar bases (as a class of impurities) and neutral oil substances (as a class of impurities) have much less a tendency to hydrogen bond with such polyhydric alcohols (polyols), thus their volatility during extractive distillation with polyols is much less affected than that of the phenols. This permits these impurities to be removed as a distillate. The phenols are removed along with the polyol as a bottoms product from the extractive distillation process, and are subsequently separated via distillation to afford the polyol for recycle and the purified phenolic fraction as a finished product.

The enhancement of relative volatility of all tar base and neutral oil impurities correlates with increasing mole fraction of polyhydric alcohol. The exact chemical identity of an impurity (and therefore its molecular structure) impacts only on the degree of separability of that impurity, but in no instance has this impact rendered a tar base or neutral oil impurity to be only marginally separable. This process is applicable to the removal of the classes of impurities known as tar bases and neutral oils from any of the cresylic acid distillate fractions, regardless of feedstock derivation (except synthetic mixtures of cresols and xylenols, which do not contain the substances known in the natural cresylic acid industry as tar bases and neutral oils).

The technique of extractive distillation with polyols is also capable of effecting separation of many of the less abundant phenolics (in a discrete cresylic acid distillate fraction) from the more abundant phenolics (the parent fraction). As the strength of the hydrogen bond formed between a phenolic substance and a polyol increases, the extent to which the volatility of the phenolic substance is depressed increases. The tendency to form a strong hydrogen bond is most pronounced for those phenolics having the least degree of steric hindrance by alkyl or alkoxy substituents around the phenolic (hydroxy) function. This principle permits the separation of a number of undesirable phenolic substances (beyond the scope of 2,6-xylenol, ortho-ethylphenol and guaiacol from meta/para-cresol) from any of the four principal cresol and xylenol distillate fractions (ortho-cresol, m/p-cresol, 2,4/2,5-xylenol and HBX). Cresol and xylenol distillate fractions from any natural feedstock can benefit from the application of this phenolic separation technique, since it is possible for all such phenolic distillate fractions to contain (at the least) some of the undesirable phenolics referred to herein.

We have found that polyhydric alcohol extractive distillation is capable of removing a significant fraction of sulfur-bearing substances from the distillate products which can be manufactured from natural cresylic acid. The odor of such products is also distinctly improved. Moreover, the color of such products is much more stable in long-term storage than the products made via prior technologies. The traditional practice has been to use additives in order to provide a product which is color stable in storage. Such additives are not necessary for products manufactured via polyhydric-alcohol extractive distillation, since the resulting products remain a very light beige color indefinitely, rather than discoloring to the much darker colors which are characteristic of the products of most earlier purification technologies.

INTRODUCTION TO THE INVENTION

The present invention concerns natural cresylic acid processing, as opposed to synthetic cresylic acid processing. The two differ significantly with regard to the nature and amounts of impurities involved.

All cresylic acid technologies developed prior to the instant process include a process step (or steps) for removal of neutral oil substances prior to the fractionation steps which are used to isolate the various distillate products. Cresylic acid, ready for fractionation, rarely contains more than 0.25% neutral oil impurities and often contains much less. The necessity for this thorough removal of neutral oil prior to fractionation is dictated by finished product specifications. Given a feedstock, such as a coal tar middle oil distillate (which usually contains more neutral oil than phenols), this neutral oil removal step must be quite effective. Given a feedstock, such as the monohydric phenols fraction from a Phenosolvan extract (which contains only about 1% to 4% neutral oil), this neutral oil removal step is still necessary, although the task put to it is less demanding.

The present process differs from all known natural cresylic acid processing in that middle oil distillates need only be subjected to an inexpensive "rough cut" process step for diminishing neutral oil content prior to fractionation; thorough removal is not needed. It also differs in that feedstocks, such as a monohydric phenols fraction from a Phenosolvan extract (which is fairly low in neutral oil content), need not be subjected to any neutral oil removal step prior to fractionation into distillates.

Given the above "rough cut" processing (or no processing at all), the five distillate products from fractionation of cresylic acid (phenol, ortho-cresol, m/p-cresol, 2,4/2,5-xylenol and high boiling xylenols) will each contain significant amounts (up to 10% or even 20%) of neutral oil contaminants. This is permissible, since each of these distillate fractions will be subjected to the instant process, an extractive distillation process, and by this means these contaminants will be removed.

In addition to neutral oil removal, all known natural cresylic acid processing also requires removal of tar bases prior to (or during) fractional distillation. The present process differs from such prior art in that the tar base removal step may be eliminated. Tar bases, in addition to significant amounts of neutral oil, can be removed via extractive distillation with a polyhydric alcohol.

Thus it can be seen that one of the more important ways in which the instant process differs from prior technologies is that it is not intended to purify a broad boiling-range mixture of phenol, cresols, ethylphenols, xylenols and $C_9$ phenols. The process is used for purification of narrow boiling-range distillate fractions derived via fractionation of wide range mixtures. Two immediate benefits are thus the option for elimination of a separate tar base removal step and a significant reduction in the severity of (or complete elimination of) the neutral oil removal step, both of which are normally required prior to subjecting natural cresylic acid to fractional distillation. By subjecting each fraction to extractive distillation with a polyhydric alcohol, the desired components of each fraction can be recovered in a form that is as pure as or more pure than that conventionally obtained.

Details of Invention

Throughout this disclosure, all references to "cresylic acid" are to a mixture of phenol, cresols, ethylphenols, xylenols and $C_9$ phenols, and all references to a natural cresylic acid distinguish that subject matter from synthetic cresylic acid.

Feedstock for the subject process comes, e.g., from tar oil distillate and/or from crude phenol (Phenosolvan extract). Given tar oil distillate as a feedstock, the process includes either single or dual solvent treating (or alternatively yet another process) to separate the bulk of the neutrals from the phenolics, but any such process for gross separation does not need to be pushed near its performance limits, since the scheme permits separation of substantial amounts of remaining neutral oil impurities from the distillate fractions via a polyhydric alcohol extractive distillation step. Given the monohydric phenols fraction of crude phenol, no such gross separation of neutral oil prior to fractionation is necessary.

In one of the embodiments of the instant process, raw cresylic acid, prepared, e.g., via single or dual solvent processing of tar oil distillate, is subjected to a fractionation step to separate phenol. Likewise, the same is done to separate the phenol fraction of depitched and dewatered crude phenol (the monohydric phenols fraction). The phenol fraction derived from tar oil distillate must be processed separately so as to include a carboxylic acids separation step. Such a step can be as simple as dissolving this phenol fraction in gas liquor (prior to the Phenosolvan extraction step). Since carboxylic acids are not easily extracted from gas liquor into isopropyl ether, the phenol from tar oil distillate can be recovered along with the phenol from crude phenol in a better state of purity. Alternatively, known (earlier) technologies can be used to remove carboxylic acids from such phenol. The bottoms products from these two phenol fractionation steps are then blended together. This blend is then fractionated, and the distillate fractions are subjected to polyhydric alcohol extractive distillation.

The present process is not limited to blending these streams. Each stream can be processed separately, or one or the other not processed at all.

The subject technology is not limited to cresylic acid materials which contain the impurities known as guaiacol and methyl-substituted guaiacols (MSG's). Raw cresylic acid materials containing only tar bases and neutral oil (as non-phenolic contaminants), from either coal or petroleum sources (or blends of the two), benefit substantially from the polyhydric alcohol extractive distillation process. In the following paragraphs, the kinds of benefits obtained are explained for each of the five natural cresylic acid distillate fractions.

1. The phenol distillate fraction from coal-derived liquids contains neutral oil contaminants, such as ketones, anisoles, benzofurans, indenes, indans, naphthalene and aliphatic hydrocarbons, and contains tar base components, such as trimethylpyrrole (unless all or part of these were removed prior to fractionation). The phenol distillate fraction obtained from petroleum-derived feedstocks also contains tar base and neutral oil contaminants (unless removed prior to fractionation). Extractive distillation of an impure phenol distillate fraction with diethylene glycol (the preferred alcohol) is capable of providing a product containing only 10 to 15 ppm of these substances in total. Aside from diethylene glycol, a number of other substances behave in a manner which is functionally similar to the behavior of diethylene glycol, and they also work well for this purification technique.

2. Ortho-cresol obtained via fractionation of coal-derived cresylic acid contains tar base impurities, such as pyridine and aniline, and neutral oil impurities, which often include hydrocarbons, such as naphthalene and ketones. Ortho-cresol obtained from petroleum-derived feedstock is also contaminated with tar bases and neutral oil (unless removed prior to fractionation). All of these substances are easily separable from ortho-cresol via polyhydric alcohol extractive distillation.

Ordinary fractional distillation is widely used in the cresylic acid industry to separate ortho-cresol from the slightly higher-boiling 2,6-xylenol. This is a difficult separation requiring a large number of theoretical stages, and, in practice, not all of the 2,6-xylenol is usually separated (although very thorough separation is desirable). The choice of reflux ratio to accomplish this separation is limited to what is practical to use in the industrial context of this step. The fact that ortho-cresol is an overhead product in this separation mandates a reflux ratio which will permit a reasonable rate of production. It is more practical to perform this primary fractionation step in a manner which is much more tolerant of the presence of 2,6-xylenol in the overhead product. In this event lower reflux ratios can be used, and such a fractionation is more efficient.

We find that it is more practical to separate the 2,6-xylenol in a subsequent polyhydric alcohol extractive distillation step. The difference in volatility between ortho-cresol and 2,6-xylenol, given a reasonable mole fraction of, e.g., glycol, is nearly as great (or equally great) as found in ordinary fractionation. The advantage of removal of 2,6-xylenol as an overhead product (along with tar bases and neutrals) via polyhydric alcohol extractive distillation is that one is not restricted to the choice of moderate reflux ratios. This is so because of the fact that the impurities (the overhead product) constitute only a small fraction of the feed. High reflux ratios can be employed without resulting in too little productivity for a given fractionation column. It is practical to use this technique to achieve removal of 2,6-xylenol to a greater extent (whatever extent one designs to achieve) than is practical with ordinary fractionation.

Although the preferred polyhydric alcohol for ortho-cresol purification is diethylene glycol, a number of other polyhydric alcohols behave in a manner which is functionally similar to the behavior of diethylene glycol, and they also work well for this purification technique.

3. The meta/para-cresol distillate fraction from coal-derived cresylic acid contains tar bases, such as alkyl-pyridines and alkyl-anilines, and often contains neutral oils, such as naphthalene, benzonitrile, ketones, alkyl-benzofurans, alkyl-indenes and partially saturated alkyl-indene and alkyl-naphthalene structures.

Unless 2,6-xylenol is permitted to be removed with the ortho-cresol in the preceding fractionation step, the feedstock used to prepare meta/para-cresol contains 2,6-xylenol. Small amounts of ortho-cresol (not completely removed via the ordinary fractionation step) are usually found. The meta/para-cresol distillate fraction also contains ortho-ethylphenol, which has a boiling point only slightly higher than that of meta/para-cresol, too close to permit economic separation via ordinary fractionation. Meta/para-cresol (m/p-cresol) also typically contains small amounts of 2,4/2,5-xylenol not completely separated by way of the ordinary fractional distillation step. Meta/para-cresol derived from North Dakota lignite contains guaiacol, a phenolic impurity. It also contains a trace of another phenolic impurity (identity unknown) which was scarcely evident until the impurities removed from m/p-cresol via glycol extractive distillation were examined.

For some meta/para-cresol end uses, any one or more of (or all of) the above phenolic isomers found in the meta/para-cresol distillate fraction are regarded as impurities. The meta/para-cresol distillate fraction from petroleum-derived feedstocks also contains tar bases and neutral oils (unless removed prior to fractionation), and is also subject to the same problems of lack of separability of ortho-ethylphenol and the other previously-described unresolved close-boiling phenolic isomers (ortho-cresol and 2,4/2,5-xylenol). It may or may not contain traces of guaiacol. That 2,6-xylenol and guaiacol can be separated from the meta/para-cresol distillate fraction via glycol extractive distillation is known. That the ortho-ethylphenol content can be diminished via the same is also known. According to the present invention, tar bases, neutral oil substances and unresolved traces of ortho-cresol (remaining from a primary fractionation step to isolate the m/p-cresol distillate fraction) are easily separated from meta/para-cresol via polyhydric alcohol extractive distillation to levels which are near or below the lower limit of detection. In addition, small amounts of 2,4/2,5-xylenol not resolved in the primary fractionation step can be removed from meta/para-cresol. Although the relative volatilities of these two xylenol substances (relative to meta/para-cresol) are marginal (given a mole fraction of glycol which is practical and economic to use in an industrial context), high reflux ratios can be economically employed. As is the case for removal of impurities via glycol extractive distillation from ortho-cresol, both the small volume of impurities relative to the feed and the fact that they are an overhead product result in the practicality of use of high reflux ratios.

Although the preferred polyhydric alcohol for m/p-cresol purification is diethylene glycol, a number of other substances behave in a manner which is functionally similar to the behavior of diethylene glycol, and they also work well for this purification technique.

There are no detectable tar bases, neutral oils or undesirable phenolic isomers in the meta/para-cresol distillate fraction which cannot be removed via polyol extractive distillation. The use of polyhydric alcohol extractive distillation to achieve a near-100% meta/-para-cresol product (or whatever purity one designs to achieve) constitutes a major advance in the application of this technology to the problems traditionally encountered with this distillate fraction.

The 2,4/2,5-xylenol distillate fraction from coal-derived cresylic acid contains numerous alkyl-pyridines and alkyl-anilines (toluidines). Among the many neutral oil substances often found in this fraction are methyl-benzonitrile, alkyl di- and tetra-hydronaphthalenes and numerous ketones.

The 2,4/2,5-xylenol fraction obtained from petroleum-derived feedstocks also contains tar base and neutral oil contaminants (unless removed prior to fractionation). All tar base and neutral oil impurities found in the 2,4/2,5-xylenol distillate fraction are easily removed from this xylenol fraction via polyhydric alcohol extractive distillation. North Dakota lignite-derived 2,4/2,5-xylenol, obtained as a carefully fractionated distillate product, contains phenolic impurities (in addition to tar bases and neutral oil). Two of these are thought to be methyl-substituted guaiacols (MSG's). Glycol extractive distillation is capable of removing these substances.

In a 2,4/2,5-xylenol distillate fraction, both meta/-para-cresol and 2,3-xylenol can be limited to low amounts (such as less than 0.5% each) by way of ordinary fractional distillation. Such makes it possible to manufacture (via glycol extractive distillation) a 99 percent minimum 2,4/2,5-xylenol product, having amounts of tar bases and neutral oils near or below the lower limit of detection, and having MSG's present in however small a concentration one designs to achieve.

Although the preferred polyhydric alcohol for purification of 2,4/2,5-xylenol is either diethylene glycol or triethylene glycol, a number of other substances behave in a manner which is functionally similar to the behavior of these glycols, and they also work well for this purification technique. These include, e.g., tetraethylene, dipropylene and tripropylene glycols; dialkanolamines, such as diethanolamine; trialkanolamines, such as triethanolamine; thiodiglycol; glycerol; and mixtures of such polyhydric alcohols. Each of these polyhydric alcohols is also useful for the other extractive distillations referred to herein. Virtually the only practical limitation of the polyhydric alcohol extractant is that it must have a boiling point sufficiently greater than that of the cresylic acid distillate fraction to permit subsequent separation of the extractant from the parent cresylic acid distillate fraction.

5. The high-boiling xylenol distillate fraction (HBX) from coal-derived cresylic acid feedstocks consists of 2,3-xylenol, 3,5-xylenol, para-ethylphenol, meta-ethylphenol, 3,4-xylenol, 4-(n-propyl)phenol, several other trimethylphenols and other $C_9$ phenolics. This distillate fraction is rich in alkyl-pyridines and other higher-boiling tar bases, and in neutral oil substances, such as me-thylnaphthalenes, methylbenzonitrile, acetophenone and numerous others. The HBX fraction obtained from petroleum-derived feedstocks is also contaminated with tar base and neutral oil impurities (unless removed prior to fractionation). All tar base and neutral oil impurities found in the HBX fraction are easily removed via polyhydric alcohol extractive distillation.

Lignite-derived HBX additionally contains methyl-substituted guaiacol (MSG) substances. Glycol extractive distillation is capable of removing these substances also. An HBX fraction can be provided (via glycol extractive distillation) such that the tar base and neutral oil content is near or below the lower limit of detection, and such that MSG's are present in whatever small concentration one designs to achieve.

Although the preferred polyhydric alcohol for purification of HBX is triethylene glycol, a number of other polyols behave in a manner which is functionally similar to the behavior of triethylene glycol, and they also work well for this purification technique.

COMPARISON TO PRIOR ART

The oldest of the cresylic acid purification technologies, extraction of phenols into caustic soda and steam stripping to remove tar bases and neutral oil substances, is the only prior technology capable of removing both classes of substances in one process step. This process, including the calcium-based systems employed for regeneration of caustic, is quite bulky and energy intensive. In an effort to become more streamlined and energy efficient, all subsequent technologies have relied upon two separate process technologies to remove these two classes of impurities.

Numerous technologies for separation of neutral oil substances have relied upon many forms of liquid extraction. Most of these technologies have been applied to tar oil distillates, rich in neutral oil. Both single-solvent and dual-solvent pairs have been employed. None of the solvent systems are capable of adequately removing tar bases. All of these systems, even when pushed to the extremes of performance, have in common a lack of efficacy for removal of the most polar of the neutral oil impurities (or neutral oil substances lacking in favorable distribution). For this reason, these methods tend to provide cresylic acid mixtures which still contain significant amounts of residual neutral oil (500 to 2,000 ppm). Finished cresylic acid product specifications have become increasingly stringent in recent times. To meet such specifications, such solvent technologies would have to be operated under relatively severe conditions.

For purposes of the present technology, any one of these liquid/liquid separation technologies is useful to achieve gross separation of neutral oil from the phenolics in tar oil distillate-type materials. The phenolic distillate fractions derived via fractionation of these materials can have as much as 20% neutral oil and still be acceptable feedstocks for the subject extractive distillation process. However, preferred feedstocks have no more than 10%, advantageously up to 5%, neutral oil content. The process advantageously accommodates feedstocks having, e.g., at least 0.3% by weight neutral oil, as well as those having a lesser amount.

With regard to neutral oil removal from a tar oil distillate-type material, the subject technology is novel in that 1. the primary neutral oil separation step need not be pushed anywhere near its performance limits (as must be done with earlier technologies), 2. it constitutes a neutral oil product "polishing" technology, a type of process step never before described,
3. the neutral oil content achieved (10 to 50 ppm, or whatever one designs to achieve) is much lower than ever described for any of the prior technologies (typical neutral oil specifications have in the past been "less than 0.25%" or perhaps "less than 0.1%") and
4. the present technology is not a technique designed to treat a broad boiling-range mixture of phenols prior to fractionation, but, instead, it is designed specifically to treat materials after fractionation, and is in this way completely unique among neutral oil removal technologies.

The monohydric phenols fraction from wastewater extract mixtures is an excellent candidate for the process technology described in this disclosure, since it is easily low enough in neutral oil content (1% to 5%). Although this is considerably lower than tar oil distillate materials, it is much too high to yield salable cresylic acid products via direct fractionation. Therefore these materials have in the past been either causticized and steamed or subjected to any of numerous combinations of two process technologies to eliminate tar bases and neutrals. Although such combinations can result in products having very low remaining traces of tar bases, they often result in products having easily detectable residual neutral oil contaminants.

Given such a monohydrics fraction as a feedstock, the subject technology is novel for reasons 2, 3 and 4 above.

Aside from the earliest "caustic steaming" methods, the various methods for removal of tar bases have relied upon the use of mineral acids in one form or another, such as distillation of phenols from a mixture of an acid and phenols, or extraction of tar bases into an aqueous acid from a solution of phenols in a solvent, or treatment of phenols with a strongly acidic cation exchange resin. These process technologies have been applied to both raw cresylic acid materials derived from tar oil distillates and to monohydric fractions from Phenosolvan extracts (or mixtures of the two). The greatest difficulty encountered with the use of acidic treatments to remove tar bases is the production of acidic tar or acidic aqueous waste streams which are difficult to remediate or dispose of, and from which it is even more difficult to recover the tar bases as a by-product. Another problem often encountered with these methods is loss of product (phenols) due to undesirable side reactions (during distillation of acids with phenols), or loss of phenols to solubility in a dilute acidic aqueous stream (either an extract or regenerant stream). Polyhydric alcohol extractive distillation, as a means for removal of tar bases, results in the production of a by-product stream which is not contaminated with tars or mineral acids, and is sufficiently concentrated in tar bases to be easily amenable to recovery of the valuable tar bases as products in their own right, an advantage not shared by any of the prior art methods.

Technologists have paid a high price for their use of acid-based techniques for tar base removal, but such was necessary to permit an advance to the solvent extraction technologies, away from the earliest process. Although the oldest technology (steam distillation of caustic solutions of phenols) separated both tar bases and neutral oil, it provided tar bases in a form which is not amenable to their recovery as by-products, and it resulted in environmentally challenging waste streams and in loss of product yield (due to the polymerization of phenols via the action of boiling them in a caustic solution and in losses in the springing step).

The subject technology for removal of tar bases is novel in that
1. tar bases are removed in the same process as residual neutral oils,
2. no acids are used (tar base salts are not formed),
3. the tar bases are provided in a concentrated form, a non-degraded form which is both easy to deal with in an environmental sense and easy to use for recovery of tar bases as by-products and
4. the loss of phenols to side reactions, so prevalent in all other tar base removal technologies, is insignificant.

With regard to the separation of undesirable phenols from their parent distillate fractions, prior technologies in the natural cresylic acid industry have focused on numerous techniques. Only two of these numerous technologies were based on glycol extractive distillation, and they were directed toward purification of the m/p-cresol fraction: one for removal of 2,6-xylenol (the Consolidation Coal patent), and the other for removal of guaiacol (Leuna Werke).

With regard to separation of unwanted phenols from their parent phenolic fraction, the subject technology is novel in that
1. 2,6-xylenol is found to be separable from ortho-cresol and
2. MSG's are found to be separable from 2,4/2,5-xylenol and from HBX.

The present technology is the only technology ever to remove all three classes of undesirable substances: neutral oils, tar bases and unwanted phenols, in one process step. Synthetic cresylic acid purification is readily distinguished from the present technology since virtually none of the impurities in synthetic products are the same as any of the hundreds of impurities found in natural cresylic acid streams. (The only known exception is one of the dozens of neutral oil substances present in the phenol distillate fraction derived from coal: methylbenzofuran; it is also one of the perhaps dozens of impurities in synthetic phenol, all the remainder of which are altogether different substances than those found in natural phenol.)

With regard to desulfurization of cresylic acid, all prior art consists of liquid/liquid extraction methods, anion exchange resin techniques or oxidation with either air, hydrogen peroxide or other oxidizing agents. No instance is found in the literature of the use of polyhydric alcohol extractive distillation as a technique for removal of sulfur bearing substances.

On the topic of color stability of cresylic acid products, all prior art consisted of the use of color stabilizing additives or treatment with activated clays. No instance has been found of the use of this technique to enhance the color stability of cresylic acid products in long term storage. On the topic of odor of cresylic acid products, no instance has been found in the literature regarding the ability of polyol extractive distillation to improve the odor of such products.

Although glycol extractive distillation has been used for removal of 2,6-xylenol and guaiacol from meta-/para-cresol, polyhydric alcohol extractive distillation has not previously been used to remove tar bases or neutral oil from any of the $C_6$ through $C_9$ cresylic acid distillate fractions derived from natural feedstocks. No example has been found in the literature of the use of polyhydric alcohol extractive distillation to remove 2,6-xylenol from ortho-cresol, to remove ortho-cresol and 2,4/2,5-xylenol from meta/para-cresol, to remove MSG's or other phenolic impurities from the 2,4/2,5-xylenol discrete distillate fraction, or to remove MSG's from the high boiling xylenols fraction.

The following examples illustrate the use of glycols in extractive distillation of different cresylic acid distillate fractions. The selected glycol is optionally replaced with any of the previously-noted polyhydric alcohols. The preferred alcohol for purification of the phenol, ortho-cresol and m/p-cresol fractions is diethylene glycol; the preferred glycol for purification of the 2,4/2,5-xylenol and HBX fractions is triethylene glycol.

The examples reflect the preferred 50 mole percent polyhydric alcohol concentration on the phenolic feed-tray; the concentration optionally varies from 10 mole percent to 90 mole percent, preferably from 50 mole percent to 75 mole percent.

The preferred operating pressure is from 100 mm Hg to 200 mm Hg, although even lower pressures (down to full vacuum) offer distinct advantages. Higher pressures are also useful, even those above atmospheric, although required separations are not as easily made at higher pressures.

Example 1: Phenol

Raw cresylic acid from a Phenosolvan extract is fractionated via conventional techniques in order to isolate the phenol fraction. This phenol distillate fraction has the analysis reflected in Table 1.

TABLE 1

| RAW PHENOL COMPOSITION | |
| --- | --- |
| Substance | Weight % |
| neutral oil group 1 | 0.020 |
| neutral oil group 2 | 0.102 |
| neutral oil group 3 | 0.098 |
| neutral oil group 4 | 0.030 |
| trimethylpyrrole | 0.04 |
| phenol | 99.37 |
| ortho-cresol | 0.17 |
| organic sulfur compounds | 0.0048 |
| water | 0.15 |

For the above analysis, the several dozen neutral oil substances present in this material have been divided into four groups of substances. Each of the substances in any one group has a similar relative volatility (relative to phenol) in the phenol/diethylene glycol system. The neutral oil groups are numbered in the order of ease of separability from phenol; group 1 substances are the least easily separated from phenol, and group 4 substances are the most easily separated.

Five drums of this material (total of 2,250 lbs.) are charged to the feed tank of a 6" diameter pilot plant continuous extractive distillation tower, and this material is fed to the 30th stage (of a 50 theoretical stage tower configuration) at the rate of 39.8 lbs. per hour. Diethylene glycol (DEG) is fed to the 46th stage at the rate of 170 lbs. per hour in order to maintain 50 mole % DEG on the phenol feed stage. The pressure profile across the structured packing is such that the overhead pressure is 99 mm Hg and the reboiler pressure is 105 mm Hg (given a boilup rate which results in a heat duty for the overhead condenser of 33,000 BTU per hour). None of the overhead product is drawn off until the liquid level in the overhead system builds volume, and then reflux is adjusted to a ratio of 346. Provision is made to remove water as a lower phase prior to reflux of the oil phase to the column. After reflux is established, 0.21 lb. per hour of overhead product is withdrawn, and 209.6 lbs. per hour of bottoms product are withdrawn. The composition of the overhead product is indicated in Table 2.

TABLE 2

| OVERHEAD PRODUCT COMPOSITION | |
| --- | --- |
| Substance | Weight % |
| neutral oil group 1 | 3.62 |
| neutral oil group 2 | 19.9 |
| neutral oil group 3 | 19.0 |
| neutral oil group 4 | 5.89 |
| trimethylpyrrole | 7.79 |
| phenol | 13.9 |
| ortho-cresol | 0.04 |
| organic sulfur compounds | 0.55 |
| water | 29.2 |

The portion of the bottoms product from this run which was collected in drums while it was in equilibrium is later fed to the 30th stage (of a 50 theoretical stage tower configuration) in order to separate the purified phenol from the DEG. The feed rate is set at 210 lbs. per hour. The pressure profile across the structured packing is such that the overhead pressure is 99 mm Hg, and the reboiler pressure is 105 mm Hg (given a boilup rate which results in a heat duty for the overhead condenser of 20,000 BTU per hour). A reflux ratio of 1 is employed. After equilibrium is reached, recycle of overhead and bottoms products back to the feed tank is terminated; 39.6 lbs. per hour of overhead product are collected, and 170.0 lbs. per hour of bottoms product are collected. The composition of the overhead product is reflected in Table 3.

TABLE 3

| OVERHEAD PRODUCT COMPOSITION | |
| --- | --- |
| Substance | Weight % |
| neutral oil group 1 | 0.0010 |
| neutral oil group 2 | <0.0001 |
| neutral oil group 3 | <0.0001 |
| neutral oil group 4 | <0.0001 |
| trimethylpyrrole | <0.0001 |
| phenol | 99.8 |
| ortho-cresol | 0.17 |
| organic sulfur compounds | 0.0019 |
| water | trace |

These test results show that thorough removal of neutral oils and tar bases and partial removal of sulfur compounds are readily accomplished by the stated extractive distillation conditions.

Example 2: Ortho-Cresol

Raw cresylic acid is fractionated via conventional continuous feed techniques in order to isolate the ortho-cresol fraction. As typical for ortho-cresol fractionation methods, 2,6-xylenol is primarily excluded from the overhead product; the majority of it remains in the bottoms product of this run. An analysis of the ortho-cresol overhead product is reflected in (Table 4).

TABLE 4

| RAW ORTHO-CRESOL COMPOSITION | |
| --- | --- |
| Substance | Weight % |
| ortho-cresol | 96.0 |
| phenol | 0.20 |
| 2,6-xylenol | 0.30 |

TABLE 4-continued

| RAW ORTHO-CRESOL COMPOSITION | |
|---|---|
| Substance | Weight % |
| naphthalene | 0.20 |
| pyridine | 1.65 |
| aniline | 1.35 |
| ketones | 0.20 |
| organic sulfur compounds | 0.0421 |

Five drums of this material (total of 2,250 lbs.) are charged to the feed tank of a 6" pilot plant continuous extractive distillation tower, and this material is fed to the 40th stage (of a 65 theoretical stage tower configuration) at the rate of 20 lbs. per hour. Diethylene glycol is fed to the 60th stage at the rate of 67 lbs. per hour in order to maintain 50 mole % glycol on the ortho-cresol feed stage. The pressure profile across the structured packing is such that the overhead pressure is 100 mm Hg, and the reboiler pressure is 106 mm Hg (given a boilup rate which results in a heat duty for the overhead condenser of 19,000 BTU per hour). A reflux ratio of 74 is employed. After equilibrium is reached, the rate at which overhead product is withdrawn levels out at 0.91 lb. per hour, and the rate at which bottoms product is withdrawn levels out at 86.1 lbs. per hour. The composition of the overhead product is shown in Table 5.

TABLE 5

| OVERHEAD PRODUCT COMPOSITION | |
|---|---|
| Substance | Weight % |
| ortho-cresol | 20.0 |
| phenol | 0.02 |
| 2,6-xylenol | 4.69 |
| naphthalene | 4.38 |
| pyridine | 29.6 |
| aniline | 36.2 |
| DEG | nil |
| ketones | 4.38 |
| organic sulfur compounds | 0.58 |

The portion of the bottoms product from this run which was collected in drums while it was in equilibrium is later fed to the 40th stage (of a 65 theoretical stage tower configuration) in order to separate the purified ortho-cresol from the diethylene glycol. The feed rate is set at 86 lbs. per hour. The pressure profile across the structured packing is such that the overhead pressure is 100 mm Hg, and the reboiler pressure is 106 mm Hg (given a boilup rate which results in a heat duty for the overhead condenser of 9,000 BTU per hour). A reflux ratio of 1.5 is employed. After equilibrium is reached, recycle of the overhead and bottoms products to the feed tank is terminated; 19.0 lbs. per hour of overhead product are collected, and 67.1 lbs. per hour of bottoms product (99.9% DEG) are collected. The composition of the overhead product is set forth in Table 6.

TABLE 6

| OVERHEAD PRODUCT COMPOSITION | |
|---|---|
| Substance | Weight % |
| neutral oils | 0.0005 |
| tar bases | <0.0001 |
| phenol | 0.21 |
| ortho-cresol | 99.7 |
| 2,6-xylenol | 0.09 |
| organic sulfur compounds | 0.0157 |

These test data reflect thorough removal of neutral oils and tar bases, and partial removal of 2,6-xylenol and sulfur compounds with the noted extractive distillation conditions.

Example 3: Ortho-Cresol

Raw cresylic acid is fractionated using conventional continuous feed fractionation equipment in order to isolate the ortho-cresol fraction. Unlike ordinary ortho-cresol fractionation techniques, 2,6-xylenol is primarily included in the overhead product (only a modest amount is present in the bottoms product). Such an approach is found to require a lower reflux ratio than a conventional approach, and permits greater productivity for the fractionation equipment. An analysis of ortho-cresol overhead product from this fractionation is reflected in Table 7.

TABLE 7

| RAW ORTHO-CRESOL COMPOSITION | |
|---|---|
| Substance | Weight % |
| ortho-cresol | 93.2 |
| phenol | 0.20 |
| 2,6-xylenol | 2.99 |
| naphthalene | 0.40 |
| pyridine | 1.65 |
| aniline | 1.35 |
| ketones | 0.20 |
| organic sulfur compounds | 0.0403 |

This Example is similar to Example 2, with the exception of the following extractive distillation conditions (to permit separation of a greater amount of 2,6-xylenol): the raw ortho-cresol is again fed at 20 lbs. per hour, but the DEG is fed at 97 lbs. per hour in order to maintain 50 mole % on the ortho-cresol feed stage. The overhead condenser heat duty is 26,000 BTU per hour, a reflux ratio of 71 is used, the overhead product flow rate is 1.63 lbs. per hour and the bottoms flow is 115.4 lbs. per hour. The composition of the overhead product is reflected is Table 8.

TABLE 8

| OVERHEAD PRODUCT COMPOSITION | |
|---|---|
| Substance | Weight % |
| ortho-cresol | 20.1 |
| phenol | 0.02 |
| 2,6-xylenol | 35.4 |
| naphthalene | 4.90 |
| pyridine | 20.3 |
| aniline | 16.5 |
| ketones | 2.45 |
| organic sulfur compounds | 0.326 |

A portion of the bottoms product from this run (collected while in equilibrium) is later fed to the tower in a manner similar to the recovery run described in the previous example, except the feed rate is 115.4 lbs. per hour, the overhead condenser duty is 11,000 BTU per hour, and the reflux ratio is 2.1; 18.3 lbs. per hour of overhead product are collected, and 97.1 lbs. per hour of bottoms product are collected. The composition of the overhead product is indicated in Table 9.

TABLE 9

| OVERHEAD PRODUCT COMPOSITION | |
|---|---|
| Substance | Weight % |
| neutral oils | 0.0004 |
| tar bases | <0.0001 |
| phenol | 0.21 |
| ortho-cresol | 99.6 |
| 2,6-xylenol | 0.13 |

TABLE 9-continued

OVERHEAD PRODUCT COMPOSITION

| Substance | Weight % |
| --- | --- |
| organic sulfur compounds | 0.0137 |

These test data show that the same product quality is provided when ortho-cresol (containing significantly greater amounts of 2,6-xylenol) is used as feedstock to the extractive distillation process. The column conditions are only modestly impacted.

Example 4: m/p-Cresol

Raw cresylic acid derived via depitching and dewatering of crude phenols (a coal process wastewater extract mixture) is fractionated via conventional techniques in order to isolate the m/p-cresol distillate fraction, an analysis of which is found in Table 10.

TABLE 10

RAW m/p-CRESOL COMPOSITION

| Substance | Weight % |
| --- | --- |
| ketone #1 | 0.25 |
| ketone #2 | 0.10 |
| 2-picoline | 0.20 |
| 2,6-lutidine | 1.06 |
| collidine | 0.23 |
| aniline | 0.20 |
| toluidines | 0.04 |
| naphthalene | 0.50 |
| guaiacol | 5.57 |
| ortho-cresol | 0.79 |
| 2,6-xylenol | 1.17 |
| m/p-cresol | 87.1 |
| unknown phenolic impurity | 0.03 |
| ortho-ethylphenol | 2.55 |
| 2,4/2,5-xylenol | 0.12 |
| organic sulfur compounds | 0.0480 |

Five drums of this material (total of 2,250 lbs.) are charged to the feed tank of a pilot plant continuous extractive distillation tower, and this material is fed to the 40th stage (of a 65 theoretical stage tower configuration) at the rate of 20 lbs. per hour. Diethylene glycol is fed to the 60th stage at a rate of 52 lbs. per hour in order to maintain 50 mole % glycol on the m/p-cresol feed stage. The pressure profile across the structured packing is such that the overhead pressure is 100 mm Hg, and the reboiler pressure is 106 mm Hg (given a boilup rate which results in a heat duty for the overhead condenser of 15,000 BTU per hour). A reflux ratio of 28.5 is employed. After equilibrium is reached, the amount of overhead product withdrawn levels out at 2.54 lbs. per hour, and the amount of bottoms product withdrawn levels out at 69.5 lbs. per hour. The composition of the overhead product is presented in Table 11.

TABLE 11

OVERHEAD PRODUCT COMPOSITION

| Substance | Weight % |
| --- | --- |
| ketone #1 | 1.97 |
| ketone #2 | 0.79 |
| 2-picoline | 1.57 |
| 2,6-lutidine | 8.25 |
| collidine | 1.97 |
| aniline | 1.57 |
| toluidines | 0.39 |
| naphthalene | 3.93 |
| guaiacol | 43.6 |
| ortho-cresol | 6.29 |
| 2,6-xylenol | 9.04 |
| m/p-cresol | 10.0 |
| unknown phenolic impurity | 0.39 |

TABLE 11-continued

OVERHEAD PRODUCT COMPOSITION

| Substance | Weight % |
| --- | --- |
| ortho-ethylphenol | 9.65 |
| 2,4/2,5-xylenol | 0.40 |
| organic sulfur compounds | 0.2245 |

A portion of the bottoms product from this run (collected while in equilibrium) is later fed to the 40th stage (of a 65 theoretical stage tower configuration) in order to separate the purified m/p-cresol from the diethylene glycol. The feed rate is set at 69.6 lbs. per hour. The pressure profile across the structured packing is such that the overhead pressure is 100 mm Hg, and the reboiler pressure is 106 mm Hg (given a boilup rate which results in a heat duty for the overhead condenser of 19,000 BTU per hour). A reflux ratio of 4.0 is employed. After equilibrium is reached, recycle of overhead and bottoms products back to the feed tank is terminated, and 17.6 lbs. per hour of overhead product are collected, and 52.0 lbs. per hour of bottoms product (99.99% diethylene glycol) are collected. The composition of the overhead product is shown in Table 12.

TABLE 12

OVERHEAD-PRODUCT COMPOSITION

| Substance | Weight % |
| --- | --- |
| neutral oils | 0.0012 |
| tar bases | 0.0007 |
| guaiacol | 0.0024 |
| ortho-cresol | 0.0006 |
| 2,6-xylenol | <0.0001 |
| m/p-cresol | 98.4 |
| ortho-ethylphenol | 1.52 |
| unknown phenolic impurity | 0.0004 |
| 2,4/2,5-xylenol | 0.06 |
| organic sulfur compounds | 0.0195 |

These data show removal of neutral oils, tar bases, ortho-cresol, 2,6-xylenol, guaiacol and an unknown phenolic impurity with the noted extractive distillation conditions.

Example 5: m/p-Cresol

This example is similar to the previous example with the exception of the following extractive distillation conditions (to permit more thorough removal of ortho-ethylphenol and 2,4/2,5-xylenol): the DEG feed rate is 65 lbs. per hour (to provide 50 mole % DEG on the m/p-cresol feed tray), the m/p-cresol feed rate is again 20 lbs. per hour, the overhead condenser duty is 19,000 BTU per hour, the reflux ratio is 31.6, the overhead product withdrawal rate is 3.0 lbs. per hour and the bottoms withdrawal rate is 82 lbs. per hour. The composition of the overhead product is indicated in Table 13.

TABLE 13

OVERHEAD PRODUCT COMPOSITION

| Substance | Weight % |
| --- | --- |
| ketone #1 | 1.67 |
| ketone #2 | 0.67 |
| 2-picoline | 1.33 |
| 2,6-lutidine | 7.00 |
| collidine | 1.67 |
| aniline | 1.33 |
| toluidines | 0.33 |
| naphthalene | 3.33 |
| guaiacol | 37.0 |
| ortho-cresol | 5.33 |

TABLE 13-continued

| OVERHEAD PRODUCT COMPOSITION | |
|---|---|
| Substance | Weight % |
| 2,6-xylenol | 7.66 |
| m/p-cresol | 19.0 |
| unknown phenolic impurity | 0.33 |
| ortho-ethylphenol | 12.62 |
| 2,4/2,5-xylenol | 0.51 |
| organic sulfur compounds | 0.231 |

A portion of the bottoms product from this run (collected while in equilibrium) is later fed to the tower in a manner similar to the recovery run described in the previous example, except: the feed rate is 82 lbs. per hour, the overhead condenser heat duty is 21,000 BTU per hour, and the reflux ratio is 4.7; 16.9 lbs. per hour of overhead product are collected, and 65 lbs. per hour of bottoms product are collected. The composition of the overhead product is reflected in Table 14.

TABLE 14

| OVERHEAD PRODUCT COMPOSITION | |
|---|---|
| Substance | Weight % |
| neutral oils | 0.0008 |
| tar bases | 0.0003 |
| guaiacol | 0.0001 |
| ortho-cresol | <0.0001 |
| m/p-cresol | 99.2 |
| ortho-ethylphenol | 0.77 |
| unknown phenolic impurity | <0.0001 |
| 2,4/2,5-xylenol | 0.02 |
| organic sulfur compounds | 0.0187 |

Example 6: m/p-Cresol of Coal Tar Oil Origin

The m/p cresol distillate fraction isolated via ordinary fractionation of a raw cresylic acid derived from coal tar oil is considerably higher in ortho-ethylphenol content. This example is provided to show that 99%+ m/p-cresol can be prepared from such a raw m/p-cresol fraction with a modest increase in severity of process conditions.

The composition of raw m/p-cresol for this example is shown in Table 15:

TABLE 15

| RAW m/p-CRESOL COMPOSITION | |
|---|---|
| Substance | Weight % |
| ketone #1 | 0.40 |
| ketone #2 | 0.15 |
| 2-picoline | 2.38 |
| 2,6-lutidine | 1.95 |
| collidine | 0.48 |
| aniline | 0.22 |
| toluidines | 0.07 |
| naphthalene | 0.60 |
| guaiacol | 7.00 |
| ortho-cresol | 0.26 |
| 2,6-xylenol | 0.20 |
| m/p-cresol | 78.9 |
| unknown phenolic impurity | 0.05 |
| ortho-ethylphenol | 5.40 |
| 2,4/2,5-xylenol | 1.80 |
| organic sulfur compounds | 0.0387 |

This example is similar to the previous example with the exception of the following extractive distillation conditions: the DEG feed rate is 78 lbs. per hour (to provide 50 mole % DEG on the m/p-cresol feedtray), the m/p-cresol feed rate is again 20 lbs. per hour, the overhead condenser duty is 25,000 BTU per hour, the reflux ratio is 26.5, the overhead product withdrawal rate is 4.64 lbs. per hour and the bottoms withdrawal rate is 93.36 lbs. per hour. The composition of the overhead product from this run is indicated in Table 16.

TABLE 16

| OVERHEAD PRODUCT COMPOSITION | |
|---|---|
| Substance | Weight % |
| ketone #1 | 1.72 |
| ketone #2 | 0.65 |
| 2-picoline | 10.3 |
| 2,6-lutidine | 8.40 |
| collidine | 2.15 |
| aniline | 0.86 |
| toluidines | 0.22 |
| naphthalene | 2.58 |
| guaiacol | 30.2 |
| ortho-cresol | 1.08 |
| 2,6-xylenol | 0.86 |
| m/p-cresol | 12.00 |
| unknown phenolic impurity | 0.22 |
| ortho-ethylphenol | 21.1 |
| 2,4/2,5-xylenol | 7.54 |
| organic sulfur compounds | 0.0984 |

A portion of the bottoms product from this run (collected while in equilibrium) is later fed to the tower in a manner similar to the recovery run in the previous example, except: the feed rate is 93.4 lbs. per hour, the overhead condenser heat duty is 21,000 BTU per hour, the reflux ratio is 5.8; 15.26 lbs. per hour of overhead product are collected, and 78 lbs. per hour of bottoms product are collected. The composition of the overhead product is shown in Table 17.

TABLE 17

| OVERHEAD PRODUCT COMPOSITION | |
|---|---|
| Substance | Weight % |
| neutral oils | 0.0017 |
| tar bases | 0.0009 |
| guaiacol | <0.0001 |
| ortho-cresol | <0.0001 |
| m/p-cresol | 99.1 |
| ortho-ethylphenol | 0.67 |
| unknown phenolic impurity | <0.0001 |
| 2,4/2,5-XYLENOL | 0.20 |
| organic sulfur compounds | 0.0159 |

Raw m/p-cresol derived from coal tar oil, high in neutral oils, tar bases and ortho-ethylphenol, is thus brought to a 99%+ state of purity.

Example 7: 2,4/2,5-Xylenol

Raw cresylic acid is fractionated via conventional techniques in order to isolate the 2,4/2,5-xylenol fraction. The feed material to this conventional fractionation step is a bottoms product from a m/p-cresol fractionation. A 100 theoretical stage continuous feed fractionation column is used for this preceding m/p-cresol fractionation step in order to remove m/p-cresol thoroughly and to provide a nearly m/p-cresol-free feedstock for fractionation of 2,4/2,5-xylenol. This 100 theoretical stage column is then used in the 2,4/2,5-xylenol step in order to separate it thoroughly from the higher-boiling xylenols and ethylphenols. An analysis of the 2,4/2,5-xylenol overhead product is shown in Table 18.

TABLE 18

| RAW 2,4/2,5-XYLENOL COMPOSITION | |
|---|---|
| Substance | Weight % |
| various neutral oil hydrocarbons | 0.56 |
| 2,6/3,4-lutidines | 0.06 |

TABLE 18-continued

RAW 2,4/2,5-XYLENOL COMPOSITION

| Substance | Weight % |
| --- | --- |
| 3-,4-,5-picolines | 0.29 |
| 2,4/2,5-lutidines | 0.26 |
| aniline | 0.55 |
| toluidines | 0.43 |
| guaiacol | 0.17 |
| m/p-cresol | 1.17 |
| 2,4/2,5-xylenol | 95.0 |
| 2,3-xylenol | 0.06 |
| MSG #1 | 0.24 |
| MSG #2 | 1.08 |
| organic sulfur compounds | 0.0820 |

Four drums of this material (total of 1,800 lbs.) are charged to the feed tank of the 6" pilot plant continuous extractive distillation tower, and this material is fed to the 40th stage (of a 65 theoretical stage tower configuration) at the rate of 20.0 lbs. per hour. Triethylene glycol (TEG) is fed to the 60th stage at the rate of 127 lbs. per hour in order to maintain 50 mole % triethylene glycol on the 2,4/2,5-xylenol feed stage. The pressure profile across the structured packing is such that the overhead pressure is 100 mm Hg and the reboiler pressure is 106 mm Hg (given a boilup rate which results in a heat duty for the overhead condenser of 14,000 BTU per hour). A reflux ratio of 55 is employed. After equilibrium is reached, 1.29 lbs. per hour of overhead product are withdrawn, and 145.7 lbs. per hour of bottoms product are withdrawn. The composition of the overhead product is indicated on Table 19.

TABLE 19

OVERHEAD PRODUCT COMPOSITION

| Substance | Weight % |
| --- | --- |
| various neutral hydrocarbons | 8.56 |
| 2,6/3,4-lutidines | 0.78 |
| 3-4,4-5-picolines | 4.66 |
| 2,4/2,5-picolines | 3.89 |
| aniline | 8.56 |
| toluidines | 7.00 |
| m/p-cresol | 0.02 |
| guaiacol | 2.34 |
| 2,4/2,5-xylenol | 42.6 |
| 2,3-xylenol | nil |
| MSG #1 | 3.67 |
| MSG #2 | 17.1 |
| organic sulfur compounds | 0.826 |

A portion of the bottoms product from this run (collected in equilibrium) is later fed to the 40th stage (of a 65 theoretical stage tower configuration) in order to separate the purified 2,4/2,5-xylenol from the triethylene glycol. The feed rate is set at 146 lbs. per hour. The pressure profile across the structured packing is such that the overhead pressure is 100 mm Hg, and the reboiler pressure is 106 mm Hg (given a boilup rate which results in a heat duty for the overhead condenser of 21,000 BTU per hour). A reflux ratio of 5 is employed. After equilibrium is reached, recycle of overhead and bottoms products back to the feed tank is terminated; 18.95 lbs. per hour of overhead product are collected, and 127.2 lbs. per hour of bottoms product (99.86% TEG) are collected. The composition of the overhead product is shown in Table 20.

TABLE 20

OVERHEAD PRODUCT COMPOSITION

| Substance | Weight % |
| --- | --- |
| neutral oils | 0.0011 |

TABLE 20-continued

OVERHEAD PRODUCT COMPOSITION

| Substance | Weight % |
| --- | --- |
| tar bases | 0.0007 |
| guaiacol | <0.0001 |
| m/p-cresol | 0.72 |
| 2,4/2,5-xylenol | 99.2 |
| MSG #1 | 0.01 |
| MSG #2 | <0.0001 |
| 2,3-xylenol | 0.0038 |
| organic sulfur compounds | 0.0287 |

Thorough removal of tar bases, neutral oils, guaiacol and MSG's, and partial removal of sulfur compounds are thus reflected.

Example 8: High Boiling Xyenols

Raw cresylic acid is fractionated via conventional techniques in order to isolate the high-boiling xylenol (HBX) distillate fraction as a bottoms product from the 2,4/2,5-xylenol run. In order to prepare this material for extractive distillation, it is distilled to separate it from high-boiling pitch-like materials. An analysis of the overhead product from this depitching distillation is found in Table 21.

TABLE 21

RAW HBX COMPOSITION

| Substance | Weight % |
| --- | --- |
| neutral oil substances | 5.51 |
| 2,4/2,5-lutidine | 1.02 |
| 2,3-lutidine | 0.25 |
| unknown tar bases | 0.72 |
| MSG #3 | 1.0 |
| MSG #4 | 5.6 |
| 2,4/2,5-xylenol | 0.1 |
| 2,3,6- + 2,4,6-trimethylphenol | 1.4 |
| 2,3/3,5-xylenol | 23.8 |
| m-ethylphenol | 15.9 |
| p-ethylphenol | 17.2 |
| 3,4-xylenol | 9.2 |
| other C9 phenols | 18.1 |
| organic sulfur compounds | 0.223 |

Four drums of this material (total of 1,800 lbs.) are charged to the feed tank of a 6" pilot plant continuous extractive distillation tower, and this material is fed to the 40th stage (of a 65 theoretical stage tower configuration) at the rate of 20 lbs. per hour. Triethylene glycol is fed to the 60th stage at the rate of 175 lbs. per hour in order to maintain 50 mole % triethylene glycol on the HBX feed stage. The pressure profile across the structural packing is such that the overhead pressure is 200 mm Hg, and the reboiler pressure is 206 mm Hg (given a boilup rate which results in a heat duty for the overhead condenser of 11,000 BTU per hour). A reflux ratio of 21.9 is employed. After equilibrium is reached, 3.15 lbs. per hour of overhead product are withdrawn, and 191.8 lbs of bottoms product are withdrawn. The composition of the overhead product is shown in Table 22.

TABLE 22

OVERHEAD PRODUCT COMPOSITION

| Substance | Weight % |
| --- | --- |
| neutral oil substances | 35.0 |
| 2,4/2,5-lutidine | 6.37 |
| 2,3-lutidine | 1.60 |
| unknown tar bases | 4.46 |
| MSG #3 | 6.37 |
| MSG #4 | 35.7 |

TABLE 22-continued

| OVERHEAD PRODUCT COMPOSITION | |
|---|---|
| Substance | Weight % |
| 2,4/2,5-xylenol | 0.64 |
| 2,3,6- + 2,4,6-trimethylphenol | 8.92 |
| 2,3- + 3,5-xylenol | nil |
| m-ethylphenol | nil |
| p-ethylphenol | nil |
| 3,4-xylenol | nil |
| other C$_9$ phenols | 0.01 |
| organic sulfur compounds | 0.851 |

A portion of the bottoms product (collected in equilibrium) is later fed to the 40th stage (of a 65 theoretical stage tower configuration) in order to separate the purified HBX from the triethylene glycol. The feed rate is set at 192 lbs. per hour. The pressure profile across the structured packing is such that the overhead pressure is 200 mm Hg, and the reboiler pressure is 206 mm Hg (given a boilup rate which results in a heat duty for the overhead condenser of 5,000 BTU per hour). A reflux ratio of 0.8 is employed. After equilibrium is reached, recycle of overhead and bottoms products back to the feed tank is terminated; 15.52 lbs. per hour of overhead product are collected, and 176.3 lbs. per hour of bottoms product (99.25% TEG) are collected. The composition of the overhead product is shown in Table 23.

TABLE 23

| OVERHEAD PRODUCT COMPOSITION | |
|---|---|
| Substance | Weight % |
| neutral oil substances | 0.0021 |
| tar bases | 0.0008 |
| MSG #3 | <0.0001 |
| MSG #4 | 0.0013 |
| 2,4/2,5-xylenol | nil |
| 2,3,6- + 2,4,6-trimethylphenol | nil |
| 2,3- + 3,5-xylenol | 30.5 |
| m-ethylphenol | 19.4 |
| p-ethylphenol | 21.0 |
| 3,4-xylenol | 5.7 |
| other C$_9$ phenols | 23.3 |
| organic sulfur compounds | 0.089 |

Thorough removal of neutral oils, tar bases, MSG's and hindered C$_9$ phenols, and partial removal of sulfur compounds are thus accomplished.

The invention and its advantages are readily understood from the foregoing description. Various changes may be made in each of the different aspects of the process without departing from the spirit and scope of the invention or sacrificing its material advantages. The hereinbefore-described process is merely illustrative of preferred embodiments of the invention.

What is claimed is:

1. A process for producing a plurality of discrete fractions from a natural cresylic acid feedstock containing at least one member selected from the group consisting of a tar base substances and neutral oil substances and mixtures thereof and producing at least one of said discrete fractions substantially free of said member comprising the steps of:
   a. fractionally distilling said feedstock to yield a plurality of discrete fractions each containing said member, said discrete fractions selected from the group consisting of a phenol fraction, an ortho-cresol fraction, a m,p-cresol fraction, a 2,4-2,5-xylenol fraction and a high boiling xylenols fraction, and
   b. separately extractively distilling at least one of said discrete fractions with a polyhydric alcohol solvent, said solvent having a boiling point sufficiently higher than said fraction with which it is used to permit subsequent separating whereby said member is separated from said fraction in said solvent, and
   c. subsequently separating said fraction from said solvent by distilling to provide a purified fraction as an overhead product and said solvent as a bottom product and recycling said solvent to step b.

2. A process as recited in claim 1 wherein said feedstock comprises from 0.3 to 20 percent by volume of said neutral oil.

3. A process as recited in claim 1 wherein said discrete fraction further includes an impurity selected from the group consisting of a sulfur-bearing impurity and a methyl-substituted guaiacol.

4. A process as recited in claim 1 wherein said discrete fraction is a 2,4-2,5-xylenol fraction further including an impurity selected from the group consisting of a methyl-substituted guaiacol and a sulfur-bearing impurity and wherein said extractive distillation separates said further included impurity.

5. A process as recited in claim 1 wherein said discrete fraction comprises said high boiling xylenols fraction and further including an impurity selected from the group consisting of a methyl-substituted guaiacol and a sulfur-bearing impurity and wherein said extractive distillation separates said further included impurity.

6. A process as recited in claim 1 wherein said polyhydric alcohol solvent is selected from the group consisting of diethylene glycol, triethylene glycol, tetraethylene glycol, dipropylene glycol, triopropylene glycol, diethanolamine, triethanolamine, thiodiglycol, glycerol and mixture thereof.

* * * * *